(12) United States Patent
Van Der Zaan-Landwehr Johan et al.

(10) Patent No.: US 10,688,314 B2
(45) Date of Patent: Jun. 23, 2020

(54) LIGHT TREATMENT DEVICE

(71) Applicant: KONINKLIJKE PHILIPS N.V., Eindhoven (NL)

(72) Inventors: Suzanne Daniëlle Van Der Zaan-Landwehr Johan, Eindhoven (NL); Simone Irene Elisabeth Vulto, Eindhoven (NL); Jacobus Petrus Johannes Van Os, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 213 days.

(21) Appl. No.: 15/031,796

(22) PCT Filed: Oct. 10, 2014

(86) PCT No.: PCT/EP2014/071727
§ 371 (c)(1),
(2) Date: Apr. 25, 2016

(87) PCT Pub. No.: WO2015/062842
PCT Pub. Date: May 7, 2015

(65) Prior Publication Data
US 2016/0243378 A1 Aug. 25, 2016

(30) Foreign Application Priority Data
Nov. 1, 2013 (EP) ..................................... 13191242

(51) Int. Cl.
*A61N 5/06* (2006.01)

(52) U.S. Cl.
CPC .... *A61N 5/0616* (2013.01); *A61N 2005/0645* (2013.01); *A61N 2005/0652* (2013.01);
(Continued)

(58) Field of Classification Search
CPC .......... A61N 5/0616; A61N 2005/0645; A61N 2005/0652; A61N 2005/0659; A61N 2005/0661; A61N 2005/0662
(Continued)

(56) References Cited

U.S. PATENT DOCUMENTS 4,603,968 A 8/1986 Schmidt
5,152,759 A * 10/1992 Parel ...................... A61F 9/008
606/17
(Continued)

FOREIGN PATENT DOCUMENTS

CN 102579188 A 7/2012
WO 2004096343 A2 11/2004
(Continued)

*Primary Examiner* — Michael W Kahelin
*Assistant Examiner* — Vynn V Huh

(57) ABSTRACT

There is provided a light treatment device (1). The device (1) comprises a carrier (11) having an opening (5) for positioning over and viewing a treatment area and a light emitter (6) for providing treatment light to the treatment area. There is also provided an attachment (3) for attaching the carrier to a patient. The device is useful as the opening can be positioned over an area where light therapy is desired, whilst viewing the area, and then held in position with the attachment. Light therapy can then be administered to the area and treatment of areas where light therapy is not desired can be avoided.

19 Claims, 6 Drawing Sheets

(52) U.S. Cl.
CPC .............. *A61N 2005/0659* (2013.01); *A61N 2005/0661* (2013.01); *A61N 2005/0662* (2013.01)

(58) Field of Classification Search
USPC ..................................... 607/88–94
See application file for complete search history.

(56) References Cited

U.S. PATENT DOCUMENTS

| | | | |
|---|---|---|---|
| 6,223,748 | B1 | 5/2001 | Chaves |
| 7,100,615 | B1 * | 9/2006 | Kert ............... A61B 19/00 607/88 |
| 2003/0130709 | A1 * | 7/2003 | D.C. ............... A61N 5/0619 607/88 |
| 2005/0010249 | A1 | 1/2005 | Minamoto |
| 2007/0021807 | A1 | 1/2007 | Kurtz |
| 2007/0208395 | A1 * | 9/2007 | Leclerc ............ A61N 5/0616 607/86 |
| 2009/0143842 | A1 * | 6/2009 | Cumbie ........... A61N 5/0616 607/88 |
| 2009/0254156 | A1 | 10/2009 | Powell |
| 2010/0152719 | A1 * | 6/2010 | Fujikawa ........ A61B 18/203 606/9 |
| 2012/0130358 | A1 * | 5/2012 | Cisel .............. A61B 18/22 606/10 |

FOREIGN PATENT DOCUMENTS

| | | |
|---|---|---|
| WO | 2008086375 A2 | 1/2008 |
| WO | 2012010861 A1 | 1/2012 |

* cited by examiner

LIGHT TREATMENT DEVICE

FIELD OF THE INVENTION

This invention relates to a light treatment device, for light therapy.

CROSS-REFERENCE TO PRIOR APPLICATIONS

This application is the U.S. National Phase application under 35 U.S.C. § 371 of International Application No. PCT/EP2014/071727, filed on Oct. 10, 2014, which claims the benefit of European Patent Application No. 13191242.0, filed on Nov. 1, 2013. These applications are hereby incorporated by reference herein.

BACKGROUND OF THE INVENTION

For the treatment of the skin with light, e.g. the treatment of Psoriasis Vulgaris, full body treatments are used. Although this guarantees that e.g. plaques of Psoriasis Vulgaris are treated, a large area of healthy skin is treated as well. Dependent on the kind of treatment, the effects of treating healthy skin can differ from seriously impacting a patient's health to less serious cosmetic effects such as hyper pigmentation.

It would be advantageous to enable specific skin sites to be selected and treated in order to minimize such side effects.

SUMMARY OF THE INVENTION

The invention is defined by the claims.
A light treatment device is provided; comprising:
a carrier having an opening for positioning over and viewing an area defined by the carrier;
an attachment for attaching the carrier to a patient; and
a light emitter for providing treatment light to the area defined by the carrier, and
a rotatable mask,
wherein the rotatable mask comprises a plurality of holes and/or transparent panels and is located between the carrier and the light emitter, to allow the position, size and/or shape of a treatment area to be selected within the area defined by the carrier, This can enable the opening to be positioned over an area where light therapy is desired, whilst viewing the area defined by the carrier, and then to be held in position with the attachment. The rotatable mask can then be used to select the treatment area within the area defined by the carrier. Light therapy can then be administered to the area. Further, treatment of areas where light therapy is not desired can be avoided.

The position relative to the light treatment device, size and/or shape of the treatment area may be adjustable. This can enable different treatment areas to be selected.

Only one of the plurality of holes and/or transparent panels may provide the treatment area.

The opening in the carrier may be a hole or it may be a transparent or translucent panel. This can prevent the treatment part from becoming contaminated with e.g. skin flakes and ointments in use.

The light emitter may comprise one or more LEDs.

The light treatment device may further comprise a cover for covering the opening and preventing emission of stray light. This can enable positioning of the device whilst viewing the treatment area when the cover is not in place and, when the cover is in place, prevent stray light from escaping whilst the treatment device is in use.

The light treatment device may also further comprise a safety device for preventing the light emitter from emitting light when the cover is not covering the opening. This can prevent accidental operation of the device when the cover is not in place.

The light treatment device may comprise a positioning part comprising the carrier, a treatment part comprising the light emitter for providing treatment light to the treatment area, and a coupling for coupling the positioning part and the treatment part together.

Skin flakes and ointments may be present on the skin. These may only contact the positioning part, and not the treatment part, such that only the positioning part requires cleaning between uses.

The coupling for coupling the positioning part and the treatment part may comprise a magnetic coupling. This can enable convenient coupling of the positioning part and the treatment part. Further, use of a magnetic coupling can help to provide increased hygiene. In particular, use of a magnetic coupling allows the provision of a treatment device 21 without the crevices, hooks, ridges, etc. that are intrinsic to some other connection methods and a smooth treatment device is easier to clean when it is contaminated by ointments, skin flakes, etc. this can be achieved by having a smooth engagement surface on the positioning part that is magnetically coupled to a smooth engagement surface on the treatment part.

The positioning part and the treatment part may each comprise at least one permanent magnet as part of the magnetic coupling.

The positioning part and the treatment part may each comprise a plurality of permanent magnets as part of the magnetic coupling. This can provide a robust coupling.

The positioning part and the treatment part may have complementary formations for preventing light from escaping between the positioning part and the treatment part when the formations are engaged. This can prevent stray light from escaping. Stray light may damage skin and/or eyes.

The light treatment device may further comprise a safety device for preventing the light emitter from emitting light when the positioning part and the treatment part are not (magnetically) coupled together. This can prevent stray light from escaping.

The attachment for attaching the positioning part to a patient may comprise a strap. This represents a particularly convenient attachment.

There is also provided a method of positioning a light treatment device, comprising aligning an opening of a carrier with a treatment area of a patient whilst viewing the treatment area through the opening. The carrier is attached to the patient. This enables a light emitter of the light treatment device to provide treatment light to the treatment area.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a light treatment device. The device comprises a carrier having an opening for positioning over and viewing a treatment area and a light emitter for providing treatment light to the treatment area. There is also provided an attachment for attaching the carrier to a patient.

FIGS. 1 to 6 show a light treatment device, indicated generally at 1.

Figure 1:
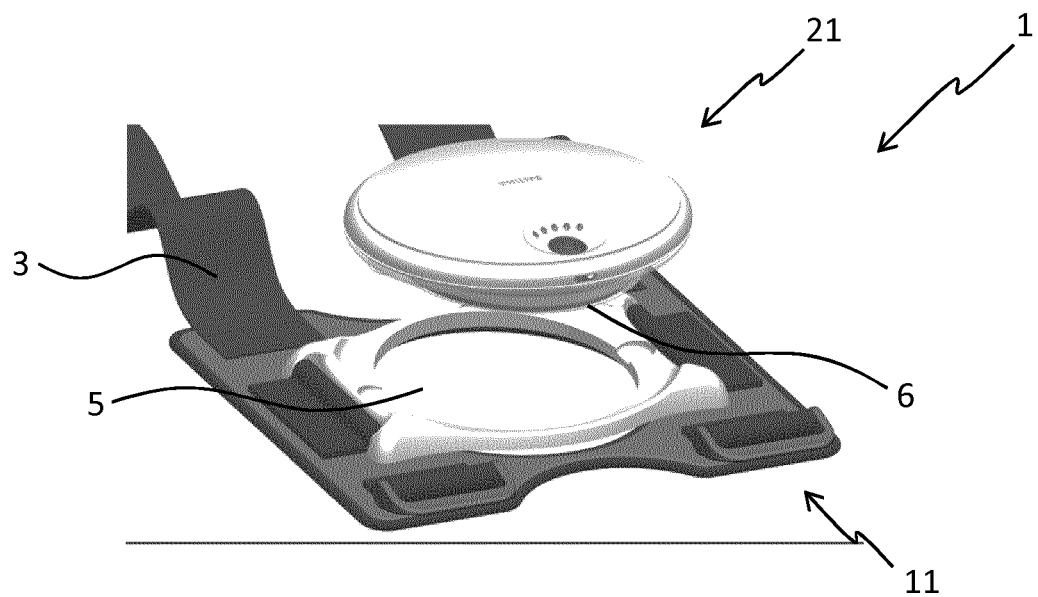
FIG. 1 shows a perspective view of a light treatment device in an unmounted position.
Figure 2:
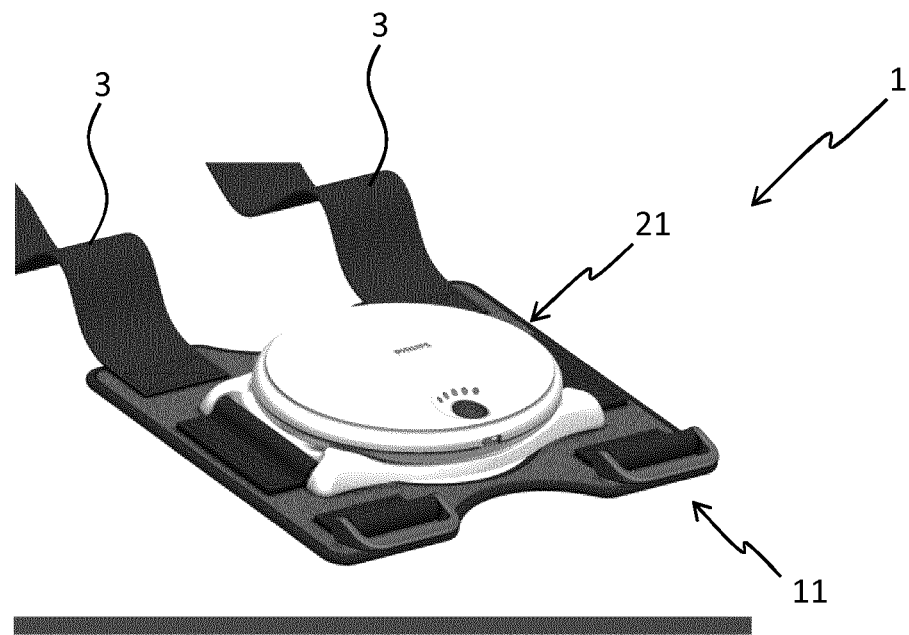
FIG. 2 shows a perspective view of the light treatment device of FIG. 1 in a different configuration where the treatment part is mounted in the intended operational position.

FIG. 1 shows a light treatment device 1 comprising a carrier 11 having an opening 5 for positioning over and viewing a treatment area. An attachment 3 for attaching the carrier 11 to a patient and a light emitter 6 for providing treatment light to the treatment area are also provided.

This can enable the opening 5 to be positioned over an area where light therapy is desired, whilst viewing the area, and then held in position with the attachment 3. Light therapy can then be administered to the area. Further, treatment of areas where light therapy is not desired can be avoided.

In the embodiment shown, the carrier 11 is a positioning part 11. The positioning part 11 comprises the attachment 3 for attaching the positioning part to the patient and the opening 5 for positioning over and viewing the treatment area. The light treatment device 1 also comprises a treatment part 21 comprising the light emitter 6 for providing treatment light to the treatment area. The light treatment device 1 also comprises a coupling 7, 9 for coupling the positioning part 11 and the treatment part 21 together (see FIGS. 5 and 6).

This can enable the opening 5 to be positioned over an area where light therapy is desired, whilst viewing the area, and then held in position with the attachment 3. With the treatment part 21 coupled to the positioning part 11 light therapy can then be administered to the area. Further, treatment of areas where light therapy is not desired can be avoided.

Skin flakes and ointments may be present on the skin. These may only contact the positioning part 11, and not the treatment part 21, such that only the positioning part 11 requires thorough cleaning between uses.

Figure 5:
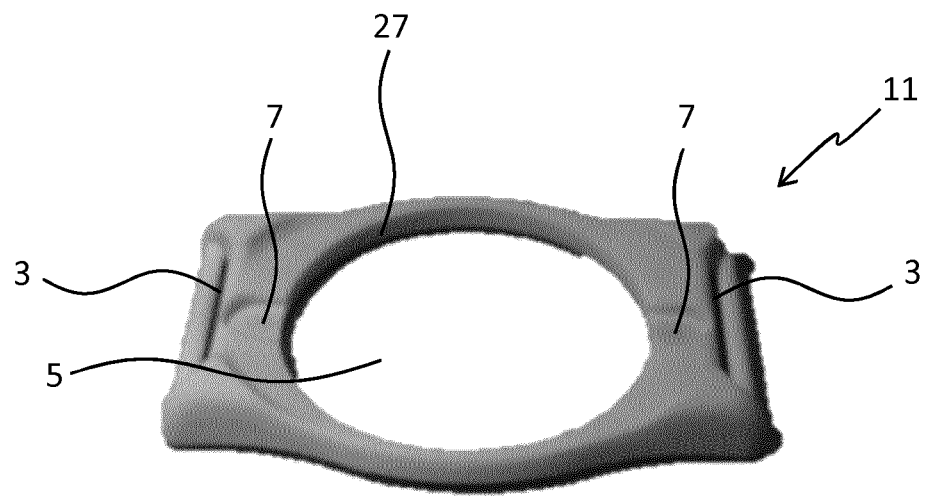
FIG. 5 shows a perspective view of a component of the positioning part of the light treatment device of FIG. 1.
Figure 6:
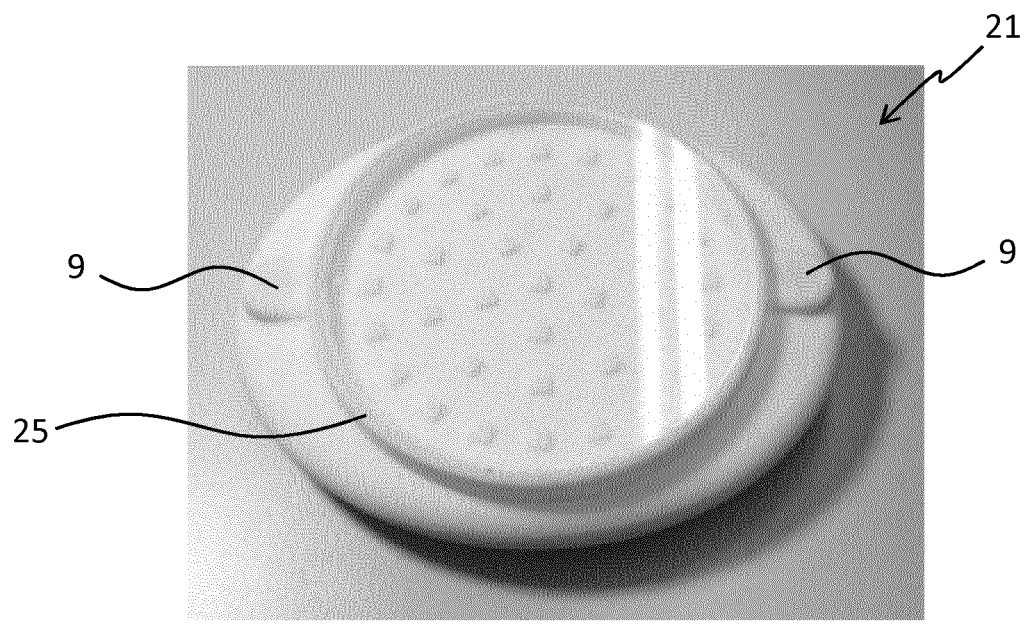
FIG. 6 shows a perspective view of the treatment part of the light treatment device of FIG. 1.

As shown in FIGS. 5 and 6 in particular, the coupling 7, 9 for coupling the positioning part 11 and the treatment part 21 is a magnetic coupling. This can enable convenient coupling of the positioning part 11 and the treatment part 21. Further, use of a magnetic coupling can help to provide increased hygiene. In particular, use of a magnetic coupling allows the provision of a treatment device 21 without the crevices, hooks, ridges, etc. that are intrinsic to some other connection methods and a smooth treatment device is easier to clean when it is contaminated by ointments, skin flakes, etc.

The positioning part 11 and the treatment part 21 each comprise a plurality of (two) permanent magnets 7, 9 as part of the magnetic coupling. This can provide a robust coupling.

Other arrangements of the magnetic coupling are possible, for example: The positioning part 11 and the treatment part 21 may each comprise one permanent magnet 7, 9 as part of the magnetic coupling. The magnetic coupling 7, 9 may comprise permanent magnets 7 in the positioning part 11 and ferromagnetic elements 9 in the treatment part 21. The magnetic coupling 7, 9 may comprise ferromagnetic elements 7 in the positioning part 11 and permanent magnets 9 in the treatment part 21. The magnetic coupling 7, 9 may comprise permanent magnets 7 in the positioning part 11 and permanent magnets 9, of appropriate polarity, in the treatment part 21.

The opening 5 is a hole.

Alternatively, the opening 5 may be a transparent or translucent panel. This can prevent the treatment part from becoming contaminated with e.g. skin flakes and ointments in use.

The positioning part 11 and the treatment part 21 are separable. This can enable the two parts to be more easily cleaned, e.g. for the positioning part 11 to be subjected to a more thorough cleaning regime.

The attachment 3 for attaching the positioning part to a patient is a strap. This represents a particularly convenient attachment.

Figure 3:
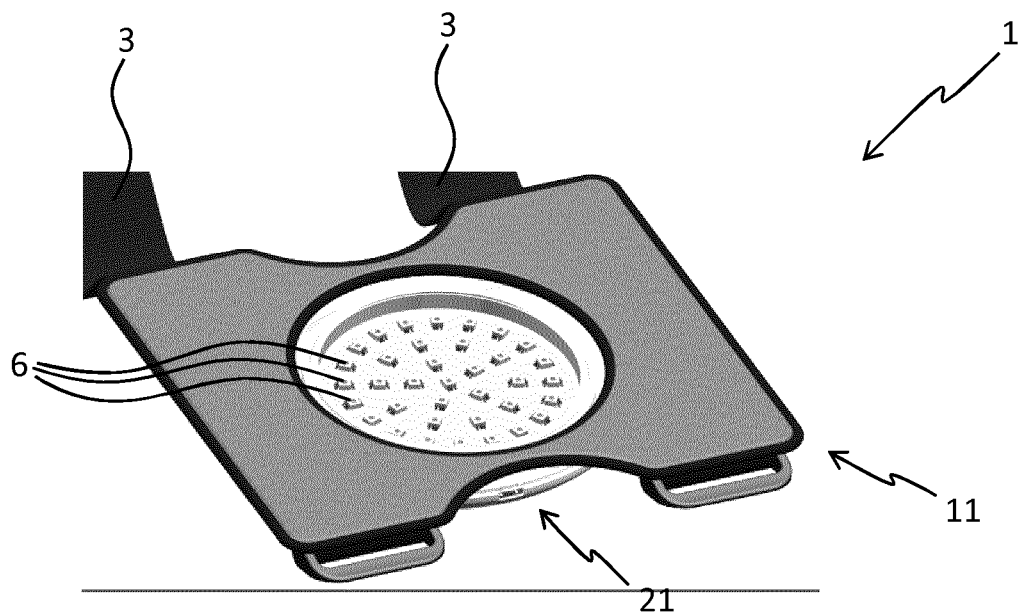
FIG. 3 shows a perspective view of the light treatment device of FIG. 1 from below.

As shown in FIG. 3 in particular, the light emitter 6 comprises a plurality of LEDs.

Figure 4:
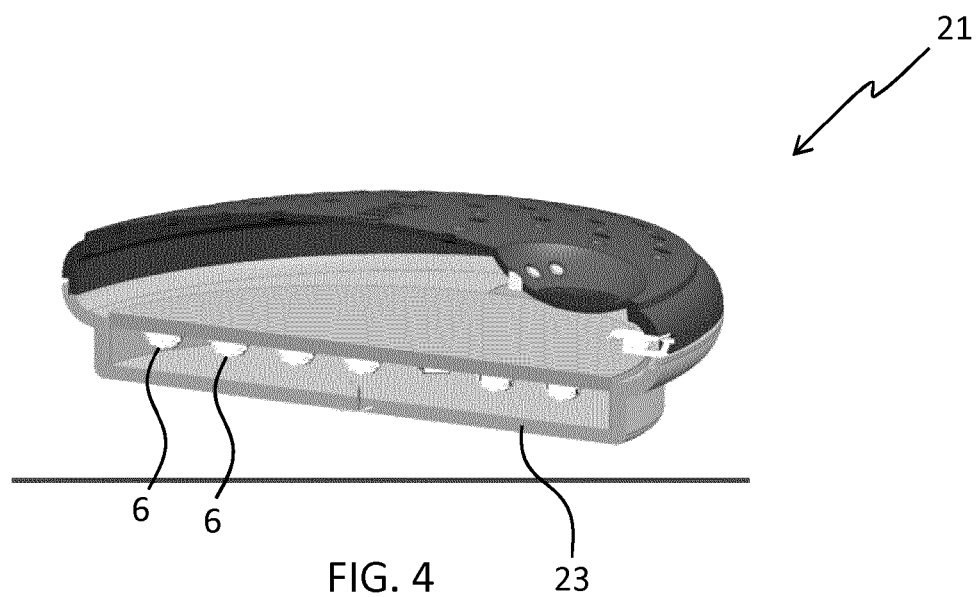
FIG. 4 shows a sectional view of a treatment part of the light treatment device of FIG. 1.

As shown in FIG. 4 in particular, the light emitter 6 may be behind a transparent or translucent cover 23.

As shown in FIGS. 5 and 6 in particular, the positioning part 11 and the treatment part 21 may have complementary formations 25, 27 for preventing light from escaping between the positioning part and the treatment part when the formations are engaged. This can prevent stray light from escaping. Stray light may damage skin and/or eyes.

The light treatment device may further comprise a safety device for preventing the light emitter from emitting light when the positioning part and the treatment part are not magnetically coupled together. This can prevent stray light from escaping.

Figure 7:
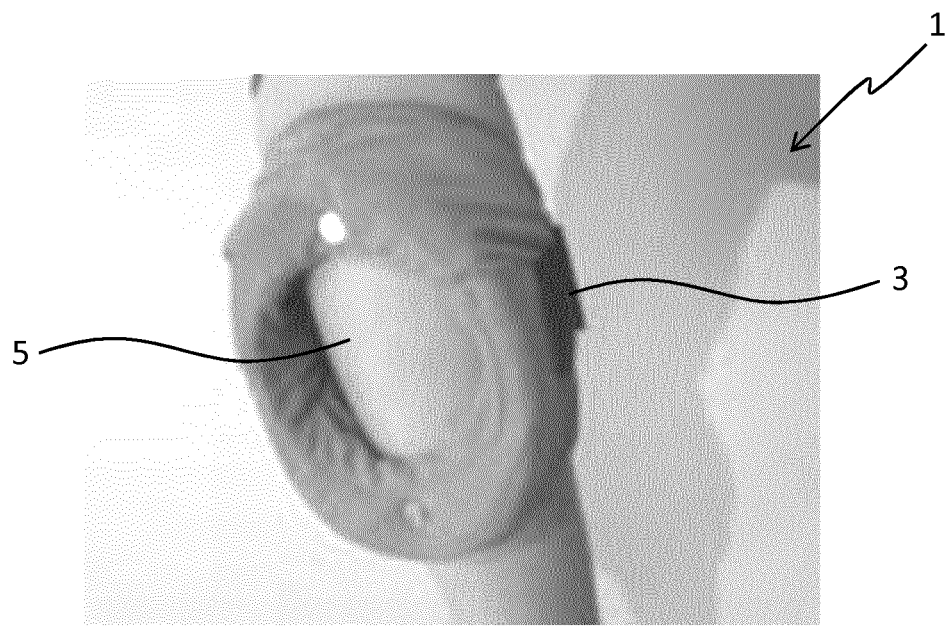
FIG. 7 shows a perspective view of a positioning part of a light treatment device in use.
Figure 8:
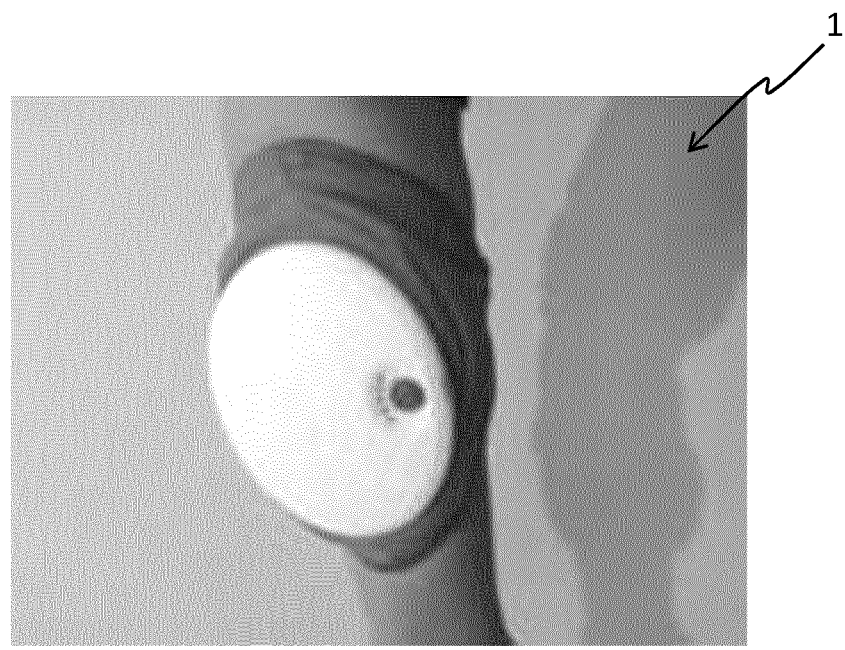
FIG. 8 shows a perspective view of a light treatment device comprising the positioning part of FIG. 7 in use.

FIGS. 7 and 8 show a light treatment device 1 in use. In FIG. 7 the opening 5 of the light treatment device 1 is positioned over a treatment area, which is viewable, and the attachment 3 is attaching the light treatment device 1 to the leg of a patient. As shown in FIG. 8 the light emitter is providing treatment light to the treatment area and no stray light is escaping.

Figure 9:
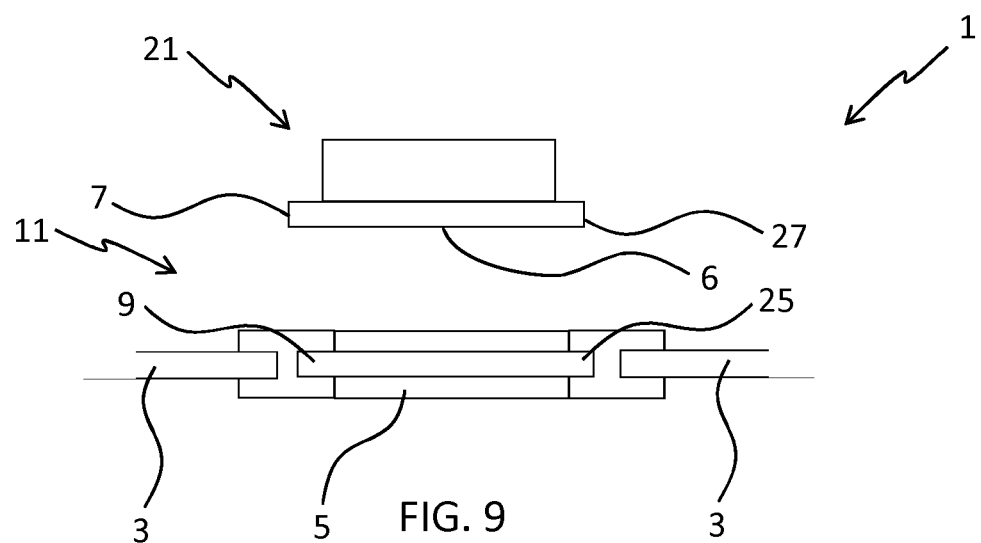
FIG. 9 shows a schematic cross sectional view of another light treatment device.

Another light treatment device is shown schematically in FIG. 9. This light treatment device, indicated generally at 1, also comprises a carrier 11 having an opening 5 for positioning over and viewing a treatment area, an attachment 3 for attaching the carrier 11 to a patient, and a light emitter 6 for providing treatment light to the treatment area.

As above, this can enable the opening 5 to be positioned over an area where light therapy is desired, whilst viewing the area, and then held in position with the attachment 3. Light therapy can then be administered to the area. Further, treatment of areas where light therapy is not desired can be avoided.

In a similar way to the light treatment device of FIGS. 1 to 6, the carrier 11 is a positioning part 11. The positioning part 11 comprises the opening 5 for positioning over and viewing the treatment area. The attachment 3 is for attaching the positioning part 11 to a patient. The light treatment device 1 also comprises a treatment part 21 comprising the light emitter 6 for providing treatment light to the treatment area. The light treatment device 1 further comprises a coupling 7, 9 for coupling the positioning part 11 and the treatment part 21 together. The coupling 7, 9 is a snap ring coupling.

This can enable the opening 5 to be positioned over an area where light therapy is desired, whilst viewing the area, and then held in position with the attachment 3. With the treatment part 21 coupled to the positioning part 11 light therapy can then be administered to the area. Further, treatment of areas where light therapy is not desired can be avoided.

Skin flakes and ointments may be present on the skin. These may only contact the positioning part 11, and not the treatment part 21, such that only the positioning part 11 requires thorough cleaning between uses.

The coupling 7, 9 for coupling the positioning part 11 and the treatment part 21 could alternatively or additionally comprise a magnetic coupling. This can enable convenient coupling of the positioning part 11 and the treatment part 21.

The opening 5 is a hole.

Alternatively, the opening 5 may be a transparent or translucent panel. This can prevent the treatment part from becoming contaminated with e.g. skin flakes and ointments in use.

The positioning part 11 and the treatment part 21 are separable. This can enable the two parts to be more easily cleaned, e.g. for the positioning part 11 to be subjected to a more thorough cleaning regime.

The light emitter 6 comprises one or more LEDs.

As shown, the positioning part 11 and the treatment part 21 have complementary formations 25, 27 for preventing light from escaping between the positioning part and the treatment part when the formations are engaged. This can prevent stray light from escaping. Stray light may damage skin and/or eyes.

The light treatment device 1 may further comprise a safety device for preventing the light emitter from emitting light when the positioning part and the treatment part are not (magnetically) coupled together. This can prevent stray light from escaping which may damage skin and/or eyes.

The attachment 3 for attaching the positioning part to a patient comprises a strap. This represents a particularly convenient attachment.

Figure 10:
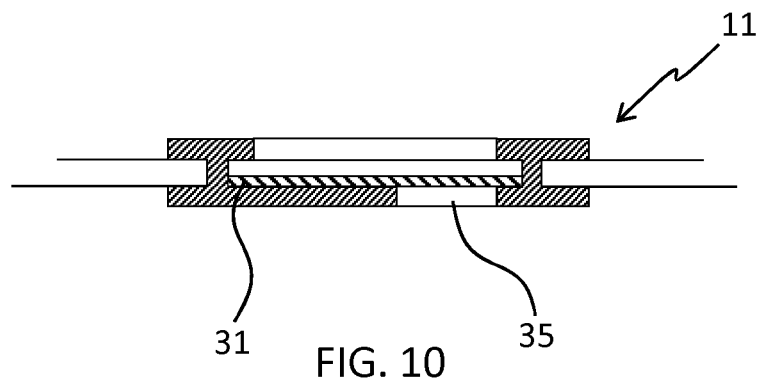
FIG. 10 shows a schematic cross sectional view of an alternative positioning part for a light treatment device.
Figure 11:
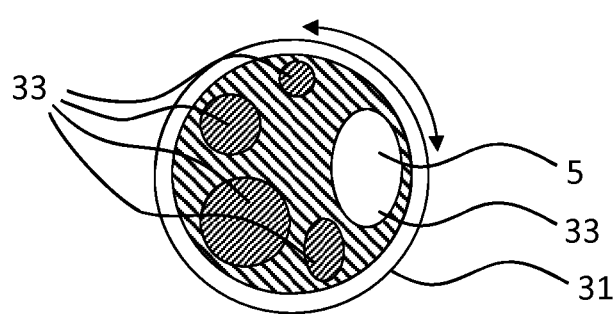
FIG. 11 shows a plan view of a mask for use in the positioning part of FIG. 10.
Figure 12:
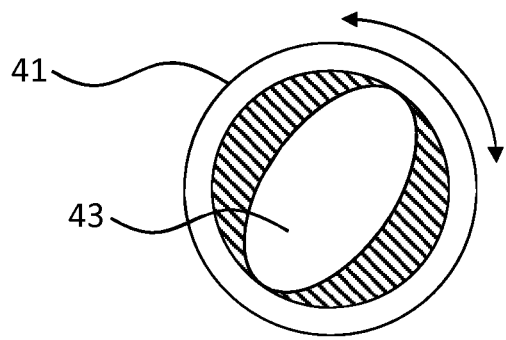
FIG. 12 shows a plan view of a mask for use in the light treatment device of FIG. 9.

Further light treatment devices and components thereof are shown schematically in FIGS. 10, 11 and 12, as the devices are similar to that of FIG. 9 the explanation focuses on the differences.

The light treatment device 1 of FIGS. 10 and 11 comprises a positioning part 11, an attachment 3 for attaching the positioning part to a patient and an opening 5 for positioning over and viewing a treatment area.

The position relative to the light treatment device 1, size and/or shape of the treatment area are adjustable. This can enable different treatment areas to be selected.

The light treatment device 1 further comprises a mask 31 having one of a plurality of holes and/or transparent panels 33 for adjusting the position, size and/or shape of the treatment area. This represents a simple arrangement for selecting the treatment area. The mask 31 sits in the snap ring coupling 9. The mask 31 is rotatably mounted.

As shown, the positioning part 11 comprises a window 35 such that only the hole and/or transparent panel 33 over the window provides a treatment area. In this way, only one of the plurality of holes and/or transparent panels 33 provides the treatment area.

As shown in FIG. 12, another light treatment device 1 comprises a mask 41 having a single hole 43 and/or transparent panel 43 for adjusting the position of the treatment area. The mask 41 sits in the snap ring coupling 9 of a device such as that of FIG. 9.

This can enable the treatment area to be turned to match the desired treatment area. The hole 43 and/or transparent panel 43 may be non-circular. The hole 43 and/or transparent panel 43 are oval shaped. The mask 41 is rotatably mounted.

Alternative masks may be provided having different sized and shaped holes and/or transparent panels for different sized and shaped treatment areas. For example, the hole 43 and/or transparent panel 43 may be positioned off-centre from the mask 41. Masks may be provided which do not initially have a hole but which are manually cut prior to use in order to match the desired treatment area.

Figure 13:
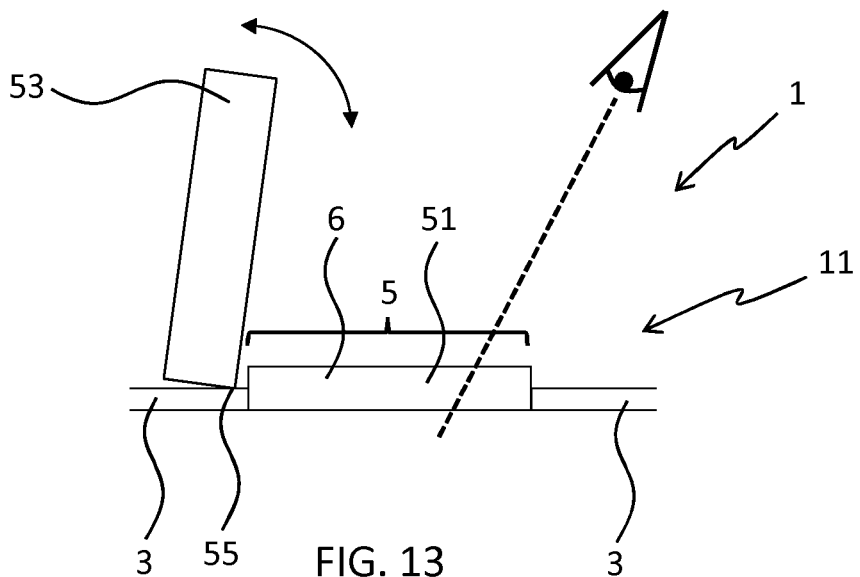
FIG. 13 shows a schematic cross sectional view of another light treatment device.
Figure 14:
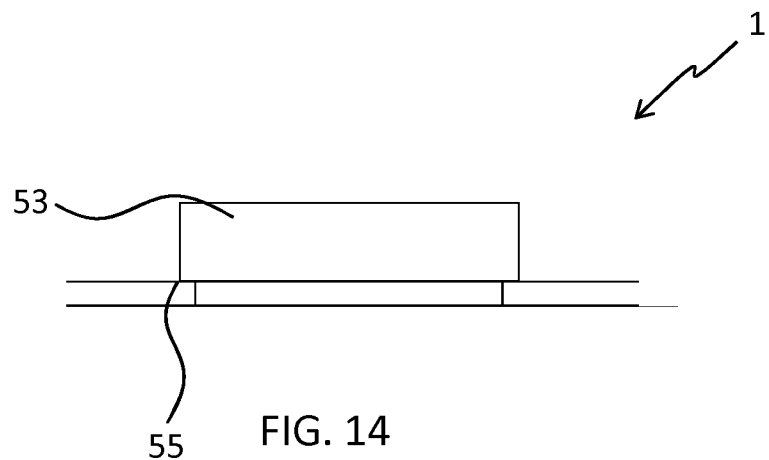
FIG. 14 shows a schematic cross sectional view of the light treatment device of FIG. 13 in a different configuration.

A further light treatment device 1 is shown in FIGS. 13 and 14. The light treatment device, indicated generally at 1, comprises a carrier 11 having an opening 5 for positioning over and viewing a treatment area. There is also provided an attachment 3 for attaching the light treatment device 1 to a patient and a light emitter 6 for providing treatment light to the treatment area are.

In this example, the light emitter 6 is formed as part of the carrier 11 rather than being removably attached to it. Furthermore, the light emitter 6 is at least partially transparent.

This can enable the opening 5 to be positioned over an area where light therapy is desired, whilst viewing the area through the light emitter 6, and then held in position with the attachment 3. Light therapy can then be administered to the area. Further, treatment of areas where light therapy is not desired can be avoided.

The light treatment device 1 comprises a transparent and/or translucent part 51 forming an opening 5 within the attachment 3. As the part 51 is transparent/translucent the treatment area is viewable through the opening 5 in which the transparent part 51 is mounted. The light emitter 6 is also formed in the transparent/translucent part 51.

The light treatment device further comprises a cover 53 for covering the opening 5 and preventing emission of stray light. This can enable positioning of the device 1 whilst viewing the treatment area through opening 5 when the cover 53 is not in place and, when the cover 53 is in place (as shown in FIG. 14), prevent stray light from escaping whilst the treatment device 1 is in use.

The cover 53 is connected to the treatment device 1 by a hinge 55.

The light treatment device 1 may also comprise a safety device for preventing the light emitter 6 from emitting light when the cover is not covering the opening. This can prevent accidental operation of the device when the cover is not in place.

The attachment for attaching the positioning part to a patient comprises a strap. This represents a particularly convenient attachment.

The device of the invention is preferably for treating relatively large regions of the body, and for this purpose the opening typically has a maximum linear dimension in the range 3 cm to 15 cm, such as a circle with diameter in this range. The attachment can be a strap as described above, for example for fixing around a limb or the torso, but other fixings can be used to hold the opening in the desired position over the area to be treated. For example, an adhesive layer can be used, similar to a plaster adhesive.

As mentioned above, the light source may be disabled when not engaged in the opening or when the light shielding lid is not closed. This can be achieved by incorporating electrical contacts into the carrier and the light emitter, or the carrier and the lid, so that an electrical circuit is formed when the light emitter is correctly engaged, or the lid is correctly closed.

The light output of the light emitter is typically in the wavelength range of from 300 nm to 1100 nm with intensities up to 100 mW/cm$^2$. The light emitter may emit UVB (280 nm to 315 nm), UVA (315 nm to 380 nm or 315 nm to 400 nm), visible (380 nm to 780 nm or 400 nm to 780 nm) and/or IR-A (780 nm to 1400 nm) light, depending on the condition to be treated. The light emitter may emit in the long-wave part of the UVB spectrum (e.g. between 300 and 320 nm or 305 nm and 315 nm), such light may be used to treat psoriasis.

Other variations to the disclosed embodiments can be understood and effected by those skilled in the art in practicing the claimed invention, from a study of the drawings, the disclosure, and the appended claims. The embodiments may be combined, for example, the masks 31, 41 of the embodiments shown in FIGS. 11 and 12 could be combined with the other embodiments shown, e.g. those of FIGS. 1 to 6 or FIGS. 13 and 14. The light source described above comprises a plurality of LEDs, however, any other light emitter which provides treatment light may be used.

In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A light treatment device comprising:
    a carrier having an opening for positioning over and viewing an area defined by the carrier;
    an attachment for attaching the carrier to a patient; and
    a treatment part comprising a light emitter for providing treatment light to the area defined by the carrier, wherein the treatment part is attached to or formed as part of the carrier, and
    a rotatable mask,
    wherein the rotatable mask comprises a plurality of holes and/or transparent panels of different sizes and/or shapes, and the rotatable mask is rotatably mounted between the carrier and the light emitter and is rotatable relative to the carrier and relative to the light emitter to allow a position, a size, and/or a shape of a treatment area to be selected within the area defined by the carrier by a rotation position of the rotatable mask with respect to the carrier.

2. The light treatment device according to claim 1, further comprising a pair of magnets for coupling the treatment part and the carrier together.

3. The light treatment device according to claim 2, wherein the pair of magnets comprises ferromagnets.

4. The light treatment device according to claim 1, wherein only a selected one of the plurality of holes and/or transparent panels of the mask provides the treatment area, the selected one of the plurality of holes and/or transparent panels of the mask being selected by the rotation position which positions the selected one of the plurality of holes and/or transparent panels of the mask over the opening of the carrier.

5. The light treatment device according to claim 1, wherein the attachment further comprises a transparent or translucent panel.

6. The light treatment device according to claim 5, wherein the light emitter comprises one or more LEDs.

7. The light treatment device according to claim 1, wherein the light treatment device comprises:
    a positioning part comprising the carrier and the attachment;
    and
    magnets for coupling the positioning part and the treatment part together.

8. The light treatment device according to claim 7, wherein the magnets include ferromagnets.

9. The light treatment device according to claim 1, wherein the rotatable mask comprises the plurality of holes and/or transparent panels of different sizes.

10. The light treatment device according to claim 1, wherein the rotatable mask comprises the plurality of holes and/or transparent panels of different shapes.

11. A method of positioning a light treatment device, comprising:
    aligning an opening of a carrier with a desired area of a patient whilst viewing an area defined by the carrier through the opening;
    attaching the carrier to the patient;
    rotatably mounting a rotatable mask onto the carrier and within an interior area of the carrier;
    rotating the rotatable mask to select a desired position, a size and/or a shape of a treatment area within the area defined by the carrier; and
    attaching a light emitter to the carrier such that the rotatable mask is positioned between the carrier and the light emitter such that the light emitter can provide treatment light to the treatment area.

12. A light treatment device comprising:
    a carrier having an opening for positioning over and viewing an area defined by the carrier;
    an attachment for attaching the carrier to a patient; and
    a treatment part comprising a light emitter for providing treatment light to the area defined by the carrier; and
    a mask which is mounted within an area in an interior of the carrier and rotatable relative to the carrier, the mask comprising one non-circular hole or transparent panel or a plurality of holes and/or transparent panels of different sizes and/or shapes, the mask being located between the carrier and the light emitter, the mask being rotatable in the carrier to allow a position, a size and/or a shape of a treatment area to be selected within the area defined by the carrier.

13. The light treatment device according to claim 12, further comprising a cover for covering the transparent panel of the attachment and preventing emission of stray light, the cover being attached to the attachment with a hinge.

14. The light treatment device according to claim 12 wherein the mask is rotatably mounted in the carrier by a snap ring coupling.

15. The light treatment device according to claim 12 wherein the carrier includes a window and the mask is rotatable in the carrier to allow the position, the size and/or the shape of the treatment area to be selected within the area defined by the one of the plurality of holes and/or transparent panels over the window of the carrier.

16. The light treatment device according to claim 12, wherein the mask comprises the plurality of holes and/or transparent panels of different sizes and/or shapes and only a selected one of the plurality of holes and/or transparent panels of the mask provides the treatment area, the selected one of the plurality of holes and/or transparent panels of the mask being selected by rotation of the mask in the carrier to position the selected one of the plurality of holes and/or transparent panels of the mask over the opening of the carrier.

17. The light treatment device according to claim 12, wherein the mask comprises the one non-circular hole or transparent panel which provides the treatment area turned by rotation of the mask to match the treatment area.

18. The light treatment device according to claim 12, wherein the mask comprises the plurality of holes and/or transparent panels of different sizes.

19. The light treatment device according to claim 12, wherein the mask comprises the plurality of holes and/or transparent panels of different shapes.

* * * * *